US00PP23634P3

(12) United States Plant Patent
Higaki

(10) Patent No.: US PP23,634 P3
(45) Date of Patent: May 28, 2013

(54) *HYDRANGEA* PLANT NAMED 'GRACE'

(50) Latin Name: ***Hydrangea macrophylla (*Thunb.)**
Varietal Denomination: Grace

(75) Inventor: Harrison M. Higaki, San Mateo, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 0 days.

(21) Appl. No.: 12/930,413

(22) Filed: Jan. 5, 2011

(65) Prior Publication Data

US 2012/0174271 P1 Jul. 5, 2012

(51) Int. Cl.
*A01H 5/00* (2006.01)

(52) U.S. Cl.
USPC ..... Plt./250

(58) Field of Classification Search ..... Plt./250
See application file for complete search history.

(56) References Cited

U.S. PATENT DOCUMENTS

PP18,266 P3 * 12/2007 de Jong ..... Plt./250
PP18,450 P2 * 1/2008 van Klaveren ..... Plt./250

* cited by examiner

*Primary Examiner* — June Hwu
(74) *Attorney, Agent, or Firm* — James R. Cypher; Charles R. Cypher

(57) ABSTRACT

A new and distinct cultivar of *Hydrangea macrophylla* (Thunb.) named 'Grace' originated as a controlled cross between unpatented varieties. The cultivar 'Grace' can be blue or red depending on the acidity of the soil and the presence of aluminum, but is preferably grown as a red variety. The variety 'Grace' has large attractive inflorescences with large sepalous florets, distinct sepal pigmentation and good tolerance to cold temperatures. The upperside of the sepals is R.H.S. 63 A (red-purple group), the underside of the sepals is R.H.S. 63 D (red-purple group)

4 Drawing Sheets

Botanical classification: *Hydrangea macrophylla* (Thunb.) 'Grace'.

Variety denomination: 'Grace'.

BACKGROUND OF THE INVENTION

This invention relates to a new and distinct cultivar of the Saxifragaceae family. The botanical name of the plant is *Hydrangea macrophylla* (Thunb.) 'Grace'.

The new cultivar originated as a seedling from a controlled cross between the unpatented variety known as 'LK49' which was the seed parent and the commercial variety 'Amsterdam'—non-patented—which was the pollen parent. 'LK49' is relatively compact plant with wiry stems, relatively small leaves, relatively small sepalous florets, and inflorescences that are resistant to being damaged by conditions in commercial coolers. 'Amsterdam' is a relatively compact plant with relatively thick stems, relatively large leaves, and medium sized sepalous florets. The inflorescences of 'Amsterdam' are not particularly resistant to being damaged by conditions in commercial coolers. The leaves or 'Grace' are similarly as large as 'Amsterdam'. The stems of 'Grace' are as strong as 'Amsterdam', and 'Grace' grows taller than either of its parents. The sepalous florets of 'Grace' are larger than either of its parents, and 'Grace' has inflorescences that are resistant to being damaged by conditions in commercial coolers like 'LK49'.

The variety 'Grace' has large attractive inflorescences with large sepalous florets, distinct sepal pigmentation and good tolerance to cold temperatures. The new variety also resists petal edge fading. The new variety resists the darkening of the sepal tips and edges as the floret ages which is typically characteristic of dark pink and red hydrangeas. Below is a table comparing the new variety to patented varieties with similar sepal pigmentation.

TABLE 1

| | New Variety 'Grace' | U.S. Plant Pat. No. 18,197 'Red Sensation' | U.S. Plant Pat. No. 18,266 'JON01' | U.S. Plant Pat. No. 18,450 'Maltisse' |
|---|---|---|---|---|
| Leaf size | 13 cm wide × 16 cm long | 4.8 cm wide × 8 cm long | 82-90 mm wide × 110-130 mm long | 8.1 cm wide × 12.6 cm long |
| Stem strength | Stems are strong but benefit from being staked | Strong | Unknown | Strong |
| Sepal Pigmentation | Upperside of sepals is R.H.S. 63 A (red-purple group); Underside of sepals is R.H.S. 63 D (red-purple group) | Upperside of sepals is R.H.S. 64 D; Underside of sepals is R.H.S. 63 C | Upperside of sepals is R.H.S. 71 B; Underside of sepals is R.H.S. 72 D | Upperside of sepals is R.H.S. 60 C; Underside of sepals is R.H.S. N57 D |
| Sepalous Floret Size | 70 mm to 100 mm | 4.5 cm | 50 mm | 4.7 cm |

The new cultivar 'Grace' has been successfully asexually reproduced under controlled environmental conditions at a nursery in Half Moon Bay, Calif. under the direction of the inventor over a three year period with its distinguishing characteristics remaining stable.

Asexual reproduction was first accomplished when vegetative cuttings were taken from the initially selected plant.

Examination of asexually reproduced, successive generations grown in at Half Moon Bay, Calif. show that the combination of characteristics as herein disclosed for 'Grace' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
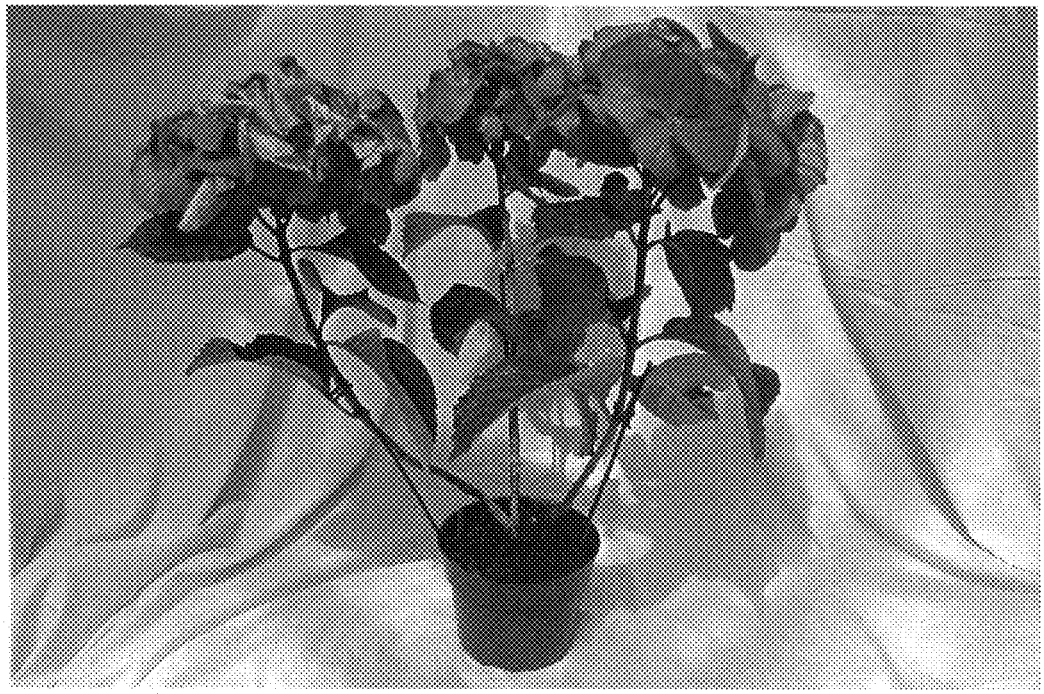
FIG. 1 is a view of the entire plant showing its form, growth habit, dark green foliage, inflorescence, and the color of its sepals.
Figure 2:
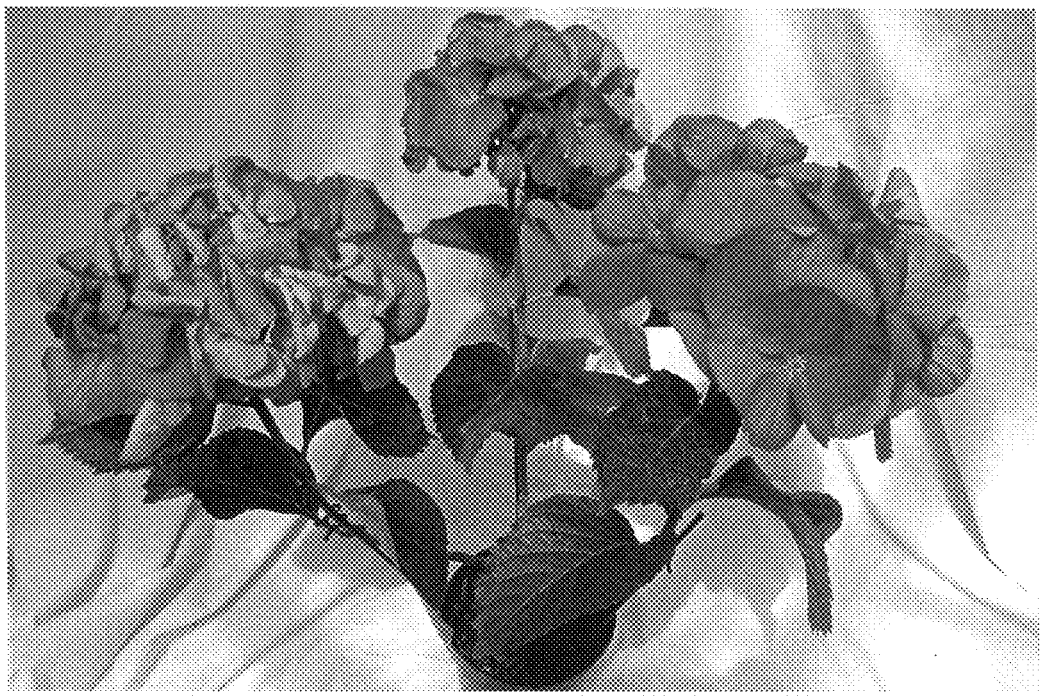
FIG. 2 is a view of the entire plant showing its form, growth habit, dark green foliage, inflorescence, and the color of its sepals.
Figure 3:
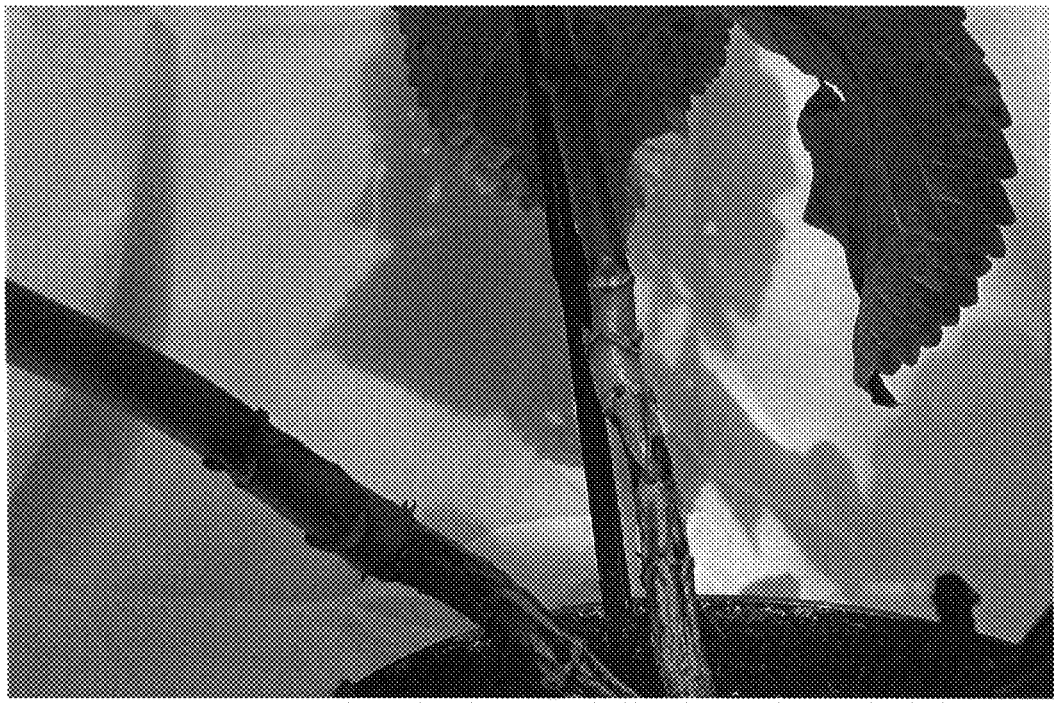
FIG. 3 is a close-up view of the base of the stem.
Figure 4:
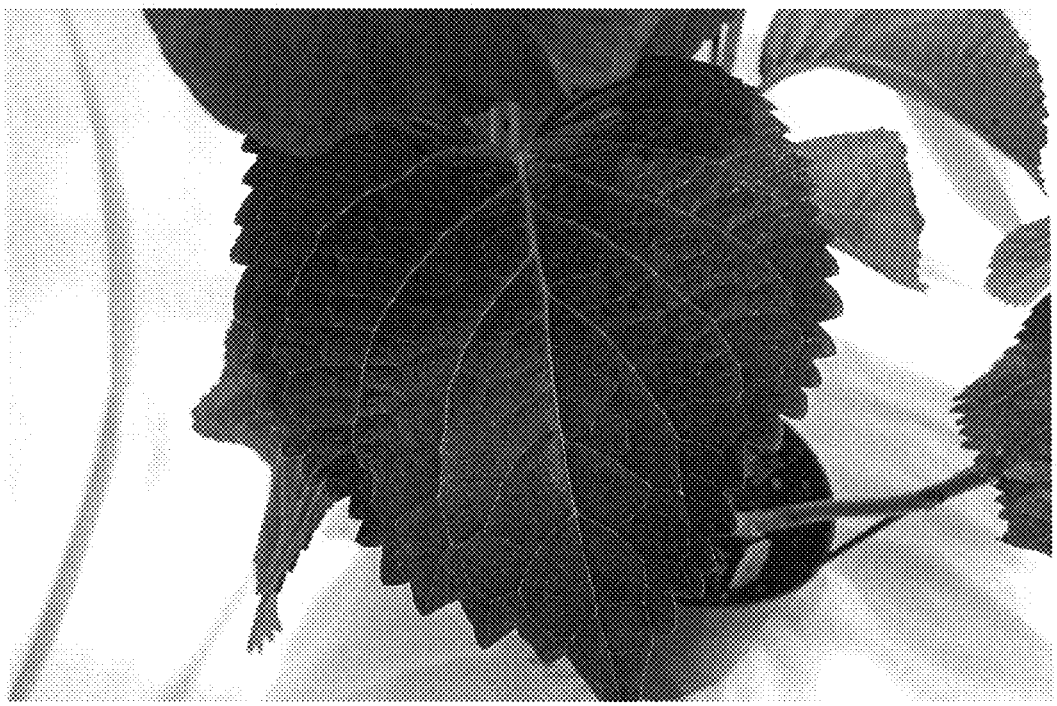
FIG. 4 is a close-up view of the adaxial surface of a mature leaf.
Figure 5:
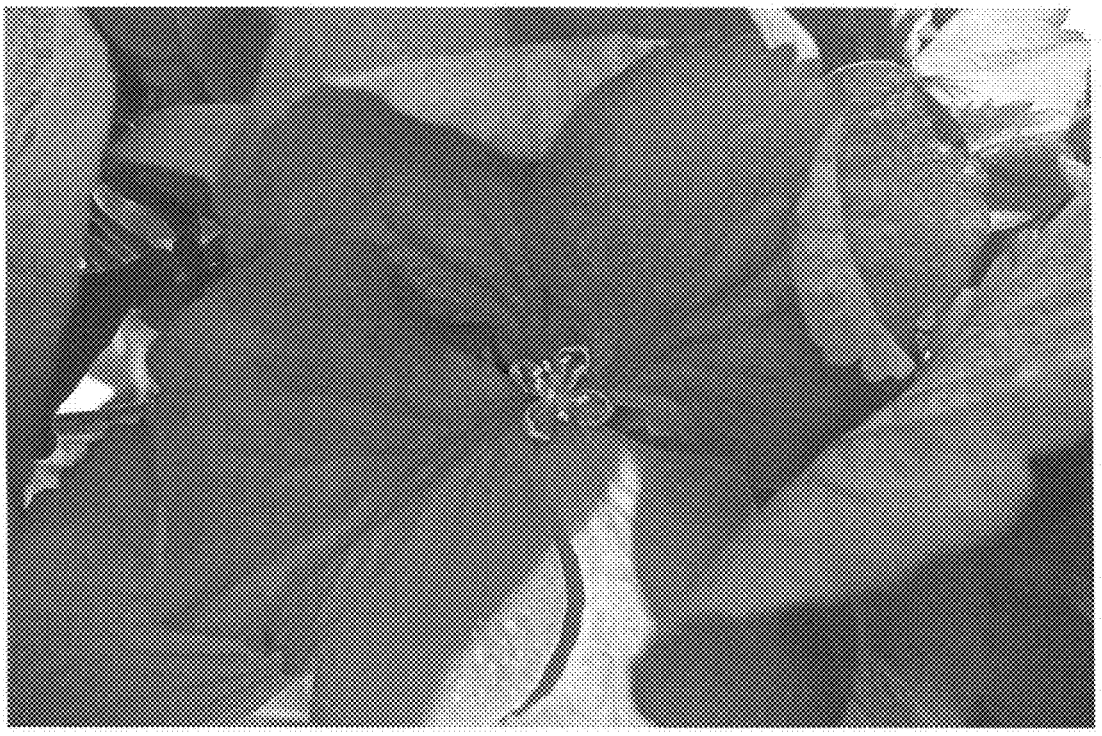
FIG. 5 is a close-up view of a sepalous floret of the new variety. The sepalous floret has opened.
Figure 6:
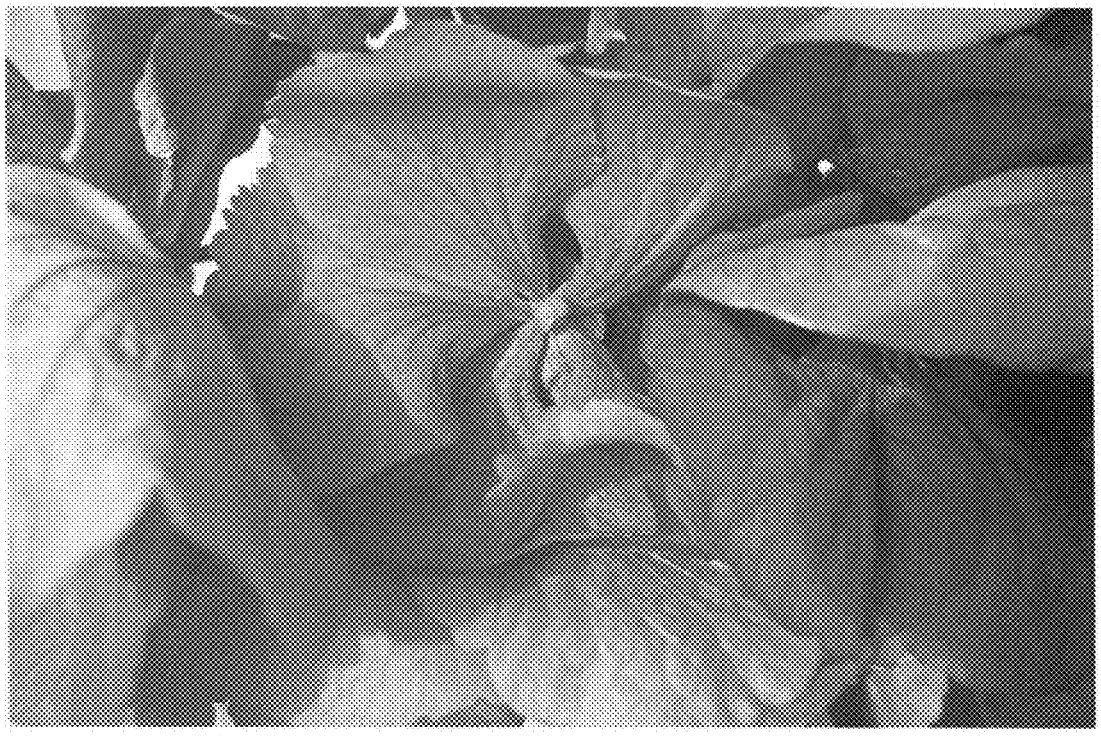
FIG. 6 is a close-up view of a sepalous floret of the new variety. The sepalous floret has not opened.
Figure 7:
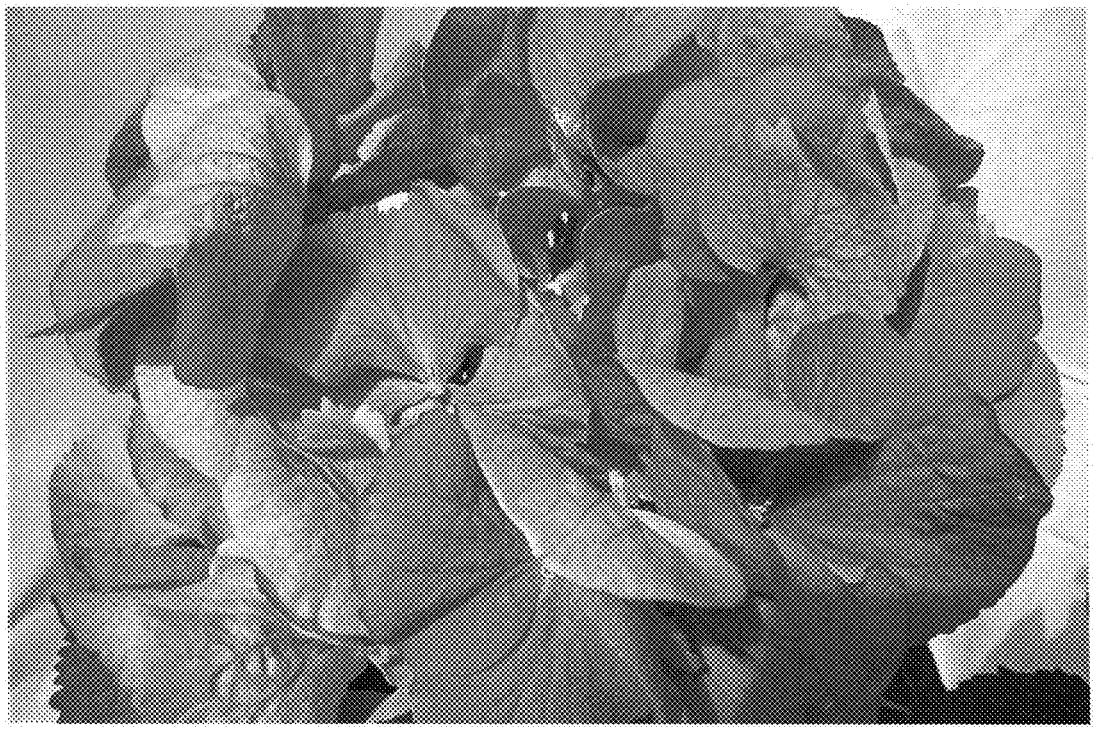
FIG. 7 is a close-up view of the upperside of a panicle of the new variety, showing opened and unopened sepalous florets.
Figure 8:
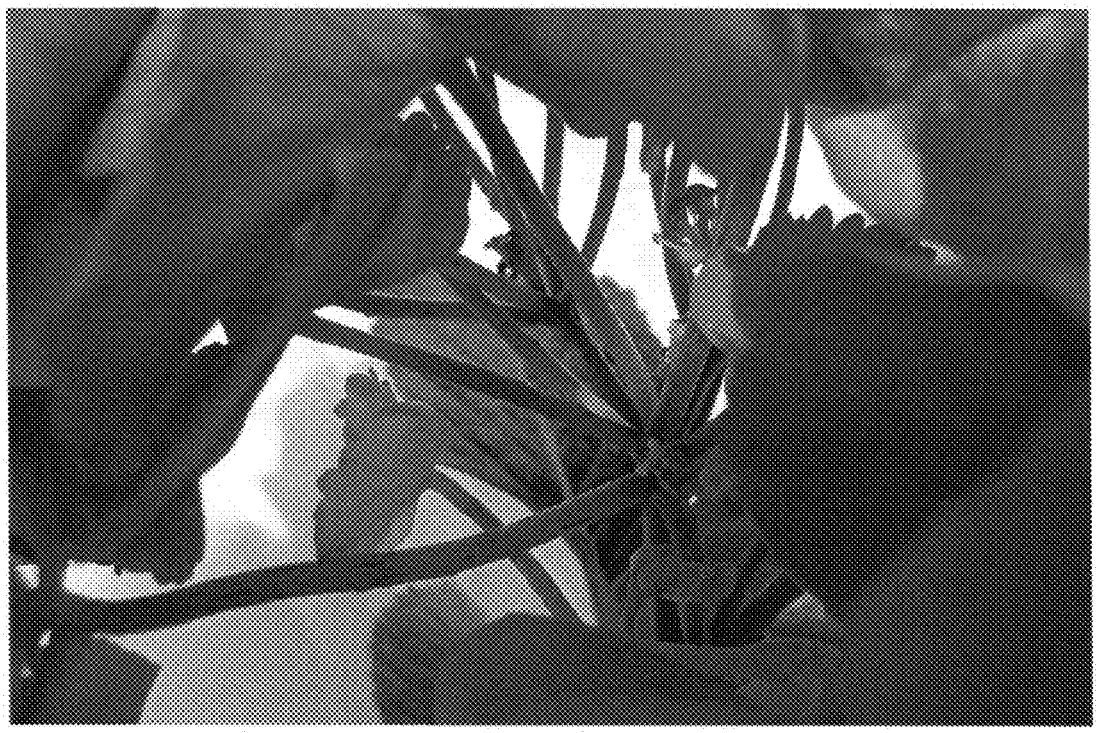
FIG. 8 is a close-up view of the center of a panicle of the new variety, showing sepalous florets and non-sepalous florets.

The plants shown in the figures are approximately 50 weeks old. The plant started out as cuttings, taken from the stem of a grown plant.

'Grace' has not been observed under all possible environmental conditions. The phenotype may vary significantly with variations in environment such as temperature, light intensity and day length. Color determinations were made with The Royal Horticultural Society (R.H.S.) Colour Chart.

THE PLANT

Origin: Controlled cross. The new cultivar originated as a seedling from a controlled cross between the unpatented variety known as LK49 which was the seed parent and the commercial variety 'Amsterdam'—non-patented—which was the pollen parent.

Form: Upright, compact shrub. A typical plant with a mature inflorescence that is ready for sale is approximately 23" high (with stakes) and has a diameter of 20" when grown in a 6" pot with appropriate soil amendments. The pictured plant had three stems with one inflorescence per stem with 1 cutting per pot.

Growth: Upright, vigorous growth habit. Inflorescence is large. The plant branches easily with shoots forming at the base of the plant. Lateral branches are similar in appearance and form to the main stems.

Stems: Lenticels are present. Lenticels are R.H.S. 86 A (violet group) and are 1 to 4 mm long. The surface of young stems is glabrous. Stems become woody as they age. The color of typical young stems and young lateral branches is R.H.S. 144 A (green group). The older portions of the stems are R.H.S. 199 C (grey-brown group) Younger portions of the stems are 7 to 9 mm thick. Older portions of the stems are 10 mm in diameter.

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the upper leaf surface.

*Color.*—Mature leaves have an upper side that is R.H.S. 147 A (yellow-green group), and an under side that is R.H.S. 138 B (green group). Leaves are pinnately veined. The midvein and veins branching off the midvein are large and prominent on the underside of the leaves. Veins are R.H.S. 138 B (green group). Leaves are as wide as 13 cm and 16 cm long. Petioles are 2.5-3.5 cm long and 4 mm wide. Petioles are smooth and R.H.S. 138 B (green group).

BUDS

Form: Globose with 3 to 5 connate, elliptic, smooth petals. Most buds, whether they will mature into sepalous or non-sepalous florets, have 4 petals. Buds in the center of the inflorescence are non-sepalous. The majority of buds will develop into sepalous florets. They are approximately 1 mm by 1 mm when very young. Buds can be 5 mm in diameter and still unopened. Buds are R.H.S. 78 B (purple group) Petals typically fall off with the reproductive organs.

Aspect: Smooth.

Arrangement: Borne on branched panicles.

INFLORESCENCE

Form: Paniculate. Terminal. As many as 100 individual flowers (florets) per inflorescence. Both sepalous florets and non-sepalous florets borne on same panicle. Flowers do not produce a fragrance. The peduncle for the inflorescence is strong and upright. Very few non-sepalous florets developing early on cymes that are later hidden by sepalous florets. Florets, both sepalous and non-sepalous, have anthers and style. Inflorescences are long-lasting.

Size of inflorescence: Large and globose. Individual inflorescence size is dependent on the number of florets. A typical inflorescence can grow as large as 9" in diameter, and 5." high.

Shape: Clusters of numerous small florets; sepalous florets overlap one another. Sepals are persistent.

Appearance: Showy.

FLORETS

General: The non-sepalous florets at the center of the inflorescence open first. Sepalous florets are perfect and complete. Corolla: Generally there are 5 petals which fall off as flower matures. Petals are typically 4 mm long and 3 mm wide. Pedicel length for non-sepalous florets averages 4 mm. Pedicel length of sepalous florets is between 30 and 40 mm in length for plants of this age. Pedicels continue to elongate as the inflorescence ages. Lenticels are present on pedicels, lenticels are no more than 1 mm long. Lenticels are R.H.S. 64 B (red-purple group) to R.H.S. 64 B (red-purple group).

Stamens: 8 stamens. Pollen is R.H.S. 155 C (white group). Plant produces abundant pollen. Filament is approximately 3 to 4 mm long. Filament is R.H.S. 155 C (white Group). Anther is 1 mm long and is regular and basally attached.

Stigma: Two to three style each, although most florets have two style. Each style has one stigma. Style is typically 2 mm long. Style is R.H.S. 155 C (white group). Stigma is R.H.S. 63 A (red-purple group).

Ovary: Ovary is partially inferior.

Sepalous florets:

*General.*—Veins dominate on the underside of the sepals.

*Number of sepals.*—4 or 5 sepals per floret, usually 4.

*Aspect of sepals.*—Smooth and glaucescent.

*Shape of sepals.*—Reniform with acuminate apex. Edges are entire, but with some crenation.

*Size of sepals.*—As the florets mature, the sepals enlarge and overlap each other more and more, until, often, there is no space between the sepals when the petals of the florets open. Sepals at maturity are typically 3.5 cm long and 3.5 cm wide. Flowers are typically 7 to 10 cm in diameter. The uppersides of the sepals are R.H.S. 63 A (red-purple group) and the undersides are R.H.S. 63 D (red-purple group).

Fruit: None.

Disease and pest resistance: Unknown.

I claim:

1. A new and distinct *Hydrangea macrophylla* plant named 'Grace' substantially as herein shown and described.

* * * * *